US012590279B2

(12) United States Patent     (10) Patent No.: US 12,590,279 B2

Ono et al.     (45) Date of Patent: Mar. 31, 2026

(54) SUBSTRATE OF CELL CULTURE CONTAINER, AND CELL CULTURE CONTAINER

(71) Applicant: AGC Inc., Tokyo (JP)

(72) Inventors: Kensuke Ono, Tokyo (JP); Kiyohisa Nakamura, Tokyo (JP); Mamoru Isobe, Tokyo (JP); Kohei Horiuchi, Tokyo (JP)

(73) Assignee: AGC Inc., Tokyo (JP)

( * ) Notice: Subject to any disclaimer, the term of this patent is extended or adjusted under 35 U.S.C. 154(b) by 581 days.

(21) Appl. No.: 18/163,341

(22) Filed: Feb. 2, 2023

(65) Prior Publication Data

US 2023/0250382 A1     Aug. 10, 2023

(30) Foreign Application Priority Data

Feb. 7, 2022    (JP) ................................. 2022-017367

(51) Int. Cl.
   *C12M 1/12*      (2006.01)
   *C12M 1/32*      (2006.01)

(52) U.S. Cl.
   CPC ............ *C12M 25/00* (2013.01); *C12M 23/12* (2013.01)

(58) Field of Classification Search
   CPC ...... C12M 25/00; C12M 23/12; C12M 23/20; C12M 23/34
   See application file for complete search history.

(56) References Cited

U.S. PATENT DOCUMENTS

2016/0312164 A1 * 10/2016 Ito .......................... C12M 33/14

FOREIGN PATENT DOCUMENTS

GB     2507744 A     5/2014

OTHER PUBLICATIONS

Journal of Bioscience and Bioengineering, Japan, The Society for Biotechnology, Japan, 2018, vol. 96, No. 7 (3 pages).

* cited by examiner

*Primary Examiner* — Michael L Hobbs

(74) *Attorney, Agent, or Firm* — Oblon, McClelland, Maier & Neustadt, L.L.P.

(57) ABSTRACT

A cell culture container has a bottom face and a surface having a dent-formed region having a plurality of dents with an average depth of 200 $\mu$m or more, the formula $\theta 1 < 90 - \theta 2 + \sin^{-1}\{\sin(\theta 2) \times 1.38/n\}$ is satisfied wherein $\theta 1$ (deg) is the angle formed by a first tangent line which passes a connecting point of a first curved line corresponding to a first dent and a second curved line corresponding to a second dent and which is in contact with the first curved line, and a base line which passes the connecting point and which is in parallel with the bottom face, and n is the refractive index of the substrate, and the formula $\theta 2 < 90 - \theta 1 + \sin^{-1}\{\sin(\theta 1) \times 1.38/n\}$ is satisfied wherein $\theta 2$ (deg) is the angle formed by a second tangent line which passes the connecting point and which is in contact with the second curved line, and the base line.

5 Claims, 5 Drawing Sheets

SUBSTRATE OF CELL CULTURE CONTAINER, AND CELL CULTURE CONTAINER

TECHNICAL FIELD

The present invention relates to a substrate of a cell culture container, and a cell culture container.

BACKGROUND ART

In a structure in which a culture solution is stored on the surface of a substrate having a plurality of fine dents formed, and cells are put in the respective dents and cultured, if the depth of the dents is not sufficient, the cells in the dents may drift out of the dents e.g. at the time of exchange of the culture solution. To prevent this, the dents may be formed on the surface of the substrate so deep as to suppress drifting (popping out) of cells (for example, Non-Patent Document 1).

PRIOR ART DOCUMENTS

Non-Patent Documents

Non-Patent Document 1: Journal of Bioscience and Bio-engineering, Japan, The Society for Biotechnology, Japan, 2018, vol. 96, No. 7, p. 384.

DISCLOSURE OF INVENTION

Technical Problem

On the other hand, if the respective dents are deep, it may be difficult to observe the cells in the dents with e.g. a microscope. Specifically, if light is applied from above the substrate toward the surface of the substrate to observe the cells, light refracted at a certain dent progresses to an adjacent dent and is reflected on the adjacent dent. The reflected light appears as a virtual image (reflection) around the adjacent dent and may impair observation of the cells in the dents or predetermined image processing of the observed image.

Under these circumstances, it is an object of the present invention to provide a substrate of a cell culture container in which cells are appropriately maintained in dents and the cells in the dents are appropriately observed, and a cell culture container provided with the substrate.

Solution to Problem

The present inventors have conducted extensive studies to achieve the above object and as a result, found that the desired effects are obtained by using the substrate of a cell culture container of the present invention and the cell culture container of the present invention, and accomplished the present invention.

That is, the present inventors have found that the above object can be achieved by the following constitution.

[1]A substrate of a cell culture container, having a bottom face and a surface provided on the opposite side from the bottom face, wherein the surface has a dent-formed region having a plurality of dents formed, the average depth of the plurality of dents is 200 μm or more, the plurality of dents includes a first dent and a second dent adjacent to each other, the nodal line of a cut surface of the substrate which passes the center of an opening of the first dent and the center of an opening of the second dent, and the first dent, has a first curved line which rises from the bottom of the first dent and extends as curved toward the second dent, the nodal line of the cut surface and the second dent has a second curved line which rises from the bottom of the second dent and extends as curved toward the first dent, the first curved line and the second curved line are connected at a connecting point, the following formula (1) is satisfied wherein $\theta 1$ (deg) is the angle formed by a first tangent line which passes the connecting point and which is in contact with the first curved line, and a base line which passes the connecting point and which is in parallel with the bottom face, and n is the refractive index of the substrate to light having a wavelength of 540 nm, and the following formula (2) is satisfied wherein $\theta 2$ (deg) is the angle formed by a second tangent line which passes the connecting point and which is in contact with the second curved line, and the base line:

$$\theta 1 < 90 - \theta 2 + \sin^{-1}\{\sin(\theta 2) \times 1.38/n\} \qquad \text{formula (1)}$$

$$\theta 2 < 90 - \theta 1 + \sin^{-1}\{\sin(\theta 1) \times 1.38/n\} \qquad \text{formula (2)}$$

[2] The substrate of a cell culture container according to [1], which is constituted by glass.

[3] The substrate of a cell culture container according to [1] or [2], wherein the size of opening of each of the plurality of dents is from 250 μm to 700 μm, and the ratio of the depth of the dent to the size of the opening of each of the plurality of dents is from 0.35 to 0.80.

[4] The substrate of a cell culture container according to any one of [1] to [3], wherein the angle $\theta 1$ and the angle $\theta 2$ are the same.

[5]A cell culture container, which comprises the substrate of a cell culture container as defined in any one of [1] to [4], and a wall member which is fixed at a position surrounding the dent-formed region on the substrate and which separates a space above the dent-formed region.

Advantageous Effects of Invention

According to the present invention, it is possible to provide a substrate of a cell culture container in which cells can appropriately be maintained in dents and the cells in the dents can appropriately be observed, and a cell culture container.

BRIEF DESCRIPTION OF DRAWINGS

FIG. 1 is an exploded view illustrating a cell culture container according to an embodiment of the present invention.

FIG. 2 is a diagram illustrating one well of a cell culture container.

FIG. 3 is an enlarged cross sectional view illustrating a well.

FIG. 4 is an enlarged plan view illustrating a dent-formed region on the surface of a substrate.

FIG. 5 is a cross sectional view illustrating the substrate cut at the A-A face of FIG. 4, and illustrates the shape of each of a first dent and a second dent.

DESCRIPTION OF EMBODIMENTS

Figure 6:
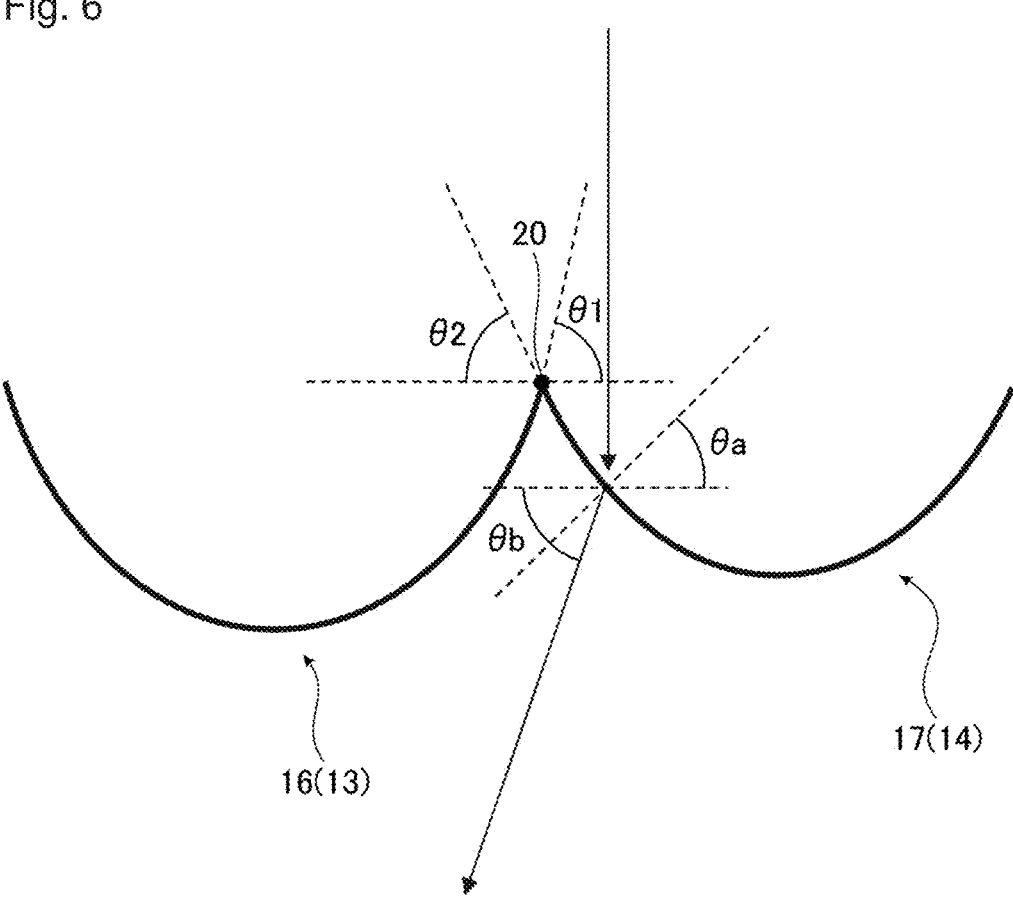
FIG. 6 is a diagram illustrating the situation in which reflection of refracted light occurs.

Now, an embodiment of the present invention will be described with reference to drawings. However, it should be understood that the embodiment described below is merely an example for easy understanding of the present invention, and the present invention is by no means restricted to such a specific embodiment. That is, various changes and modifications of the following embodiment are possible within a range not to depart from the scope of the invention.

Further, the material, the shape, etc. of the respective members used to conduct the present invention can optionally be set depending upon the application of the present invention, the technical level at the time the present invention is applied, etc. Further, the present invention includes its equivalents.

In this specification, "to" used to show the range of the numerical values is used to include the numerical values before and after it as the lower limit value and the upper limit value.

In this specification, "orthogonal", "perpendicular", "vertical", "parallel" and "horizontal" include errors within a range acceptable in the technical field to which the present invention belongs.

In this specification, a "cut surface" means a cut surface observed with a field emission scanning electron microscope manufactured by Hitachi High-Tech Corporation (hereinafter referred to as SEM) with 100 times magnification.

[Example of Constitution of Cell Culture Container]

Figure 1:
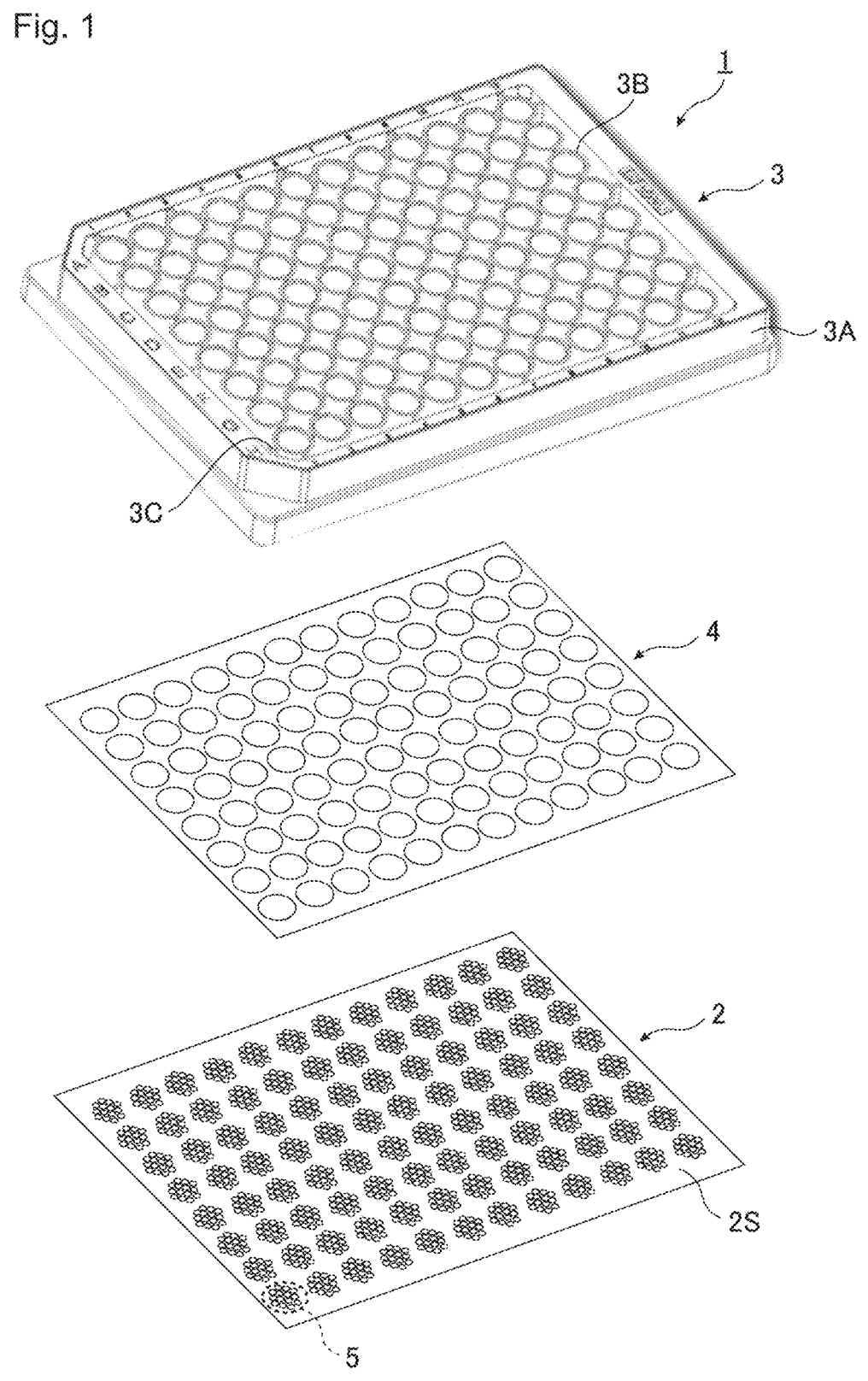
Figures 2, 3:
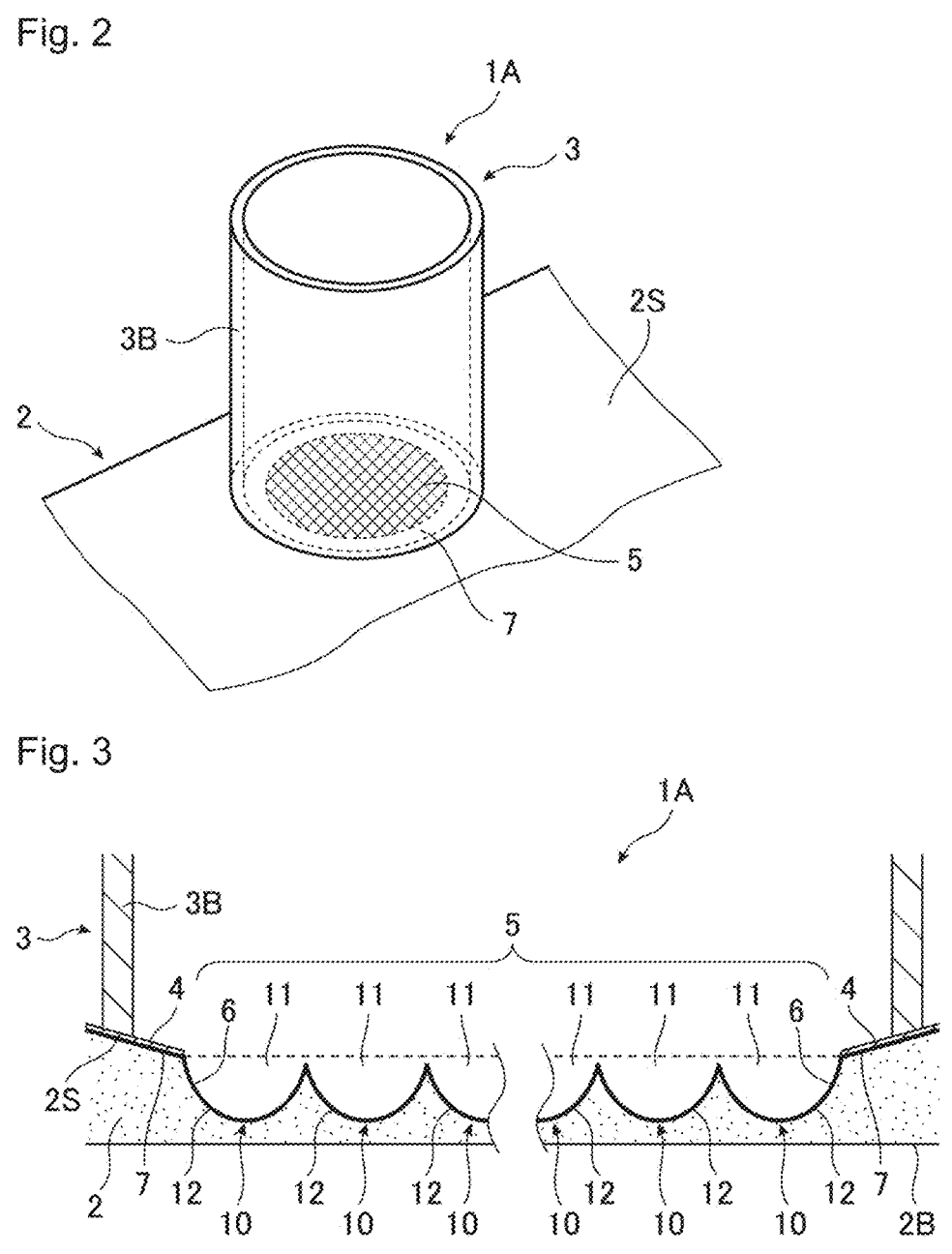

The cell culture container according to an embodiment of the present invention (hereinafter referred to as cell culture container 1) is a rectangular equipment as viewed two-dimensionally, is composed of a substrate 2 and a wall member 3 as shown in FIGS. 1 and 2, and is provided with one well 1A or more. The well 1A is, as shown in FIG. 2, a tubular space provided for cell culture, and the upper end of the well 1A is open and the lower end of the well 1A is closed by the substrate 2. During the cell culture, in the interior of the well 1A, a predetermined amount of a culture solution (most of which is constituted by water) constituting a culture medium is stored and is changed at an appropriate frequency.

In the cell culture container 1, as shown in FIGS. 2 and 3, the substrate 2 constitutes a bottom face of the container, and the wall member 3 is disposed on a surface 2S of the substrate 2 and constitutes a wall to separate the well 1A. Between the surface 2S of the substrate 2 and the wall member 3, an adhesive layer 4 selected from a pressure-sensitive adhesive tape and an adhesive is present, by which the wall member 3 is fixed to the substrate 2.

As a specific example of the adhesive, an adhesive "SE9140RTV" manufactured by DOW TORAY CO., LTD. may be mentioned.

As a specific example of the pressure-sensitive adhesive tape, a PET-based double-sided tape "5610" manufactured by Nitto Denko Corporation may be mentioned.

The bonding surface of the substrate 2 and the wall member 3 may be subjected to corona discharge treatment, so as to improve wettability by the adhesive.

The substrate 2 is constituted by a rectangular glass plate as viewed two dimensionally. The lengths of the long side and the short side of the substrate 2 are not particularly limited. Further, the thickness of the substrate 2 is also not particularly limited and may, for example, be from 0.33 mm to 0.43 mm. The substrate 2 has two principal surfaces in parallel with each other in its thickness direction. One principal surface is the surface 2S located on the side on which the wall member 3 is attached. The other principal surface is a flat bottom face 2B located on the opposite side from the surface 2S.

Figures 4, 5:
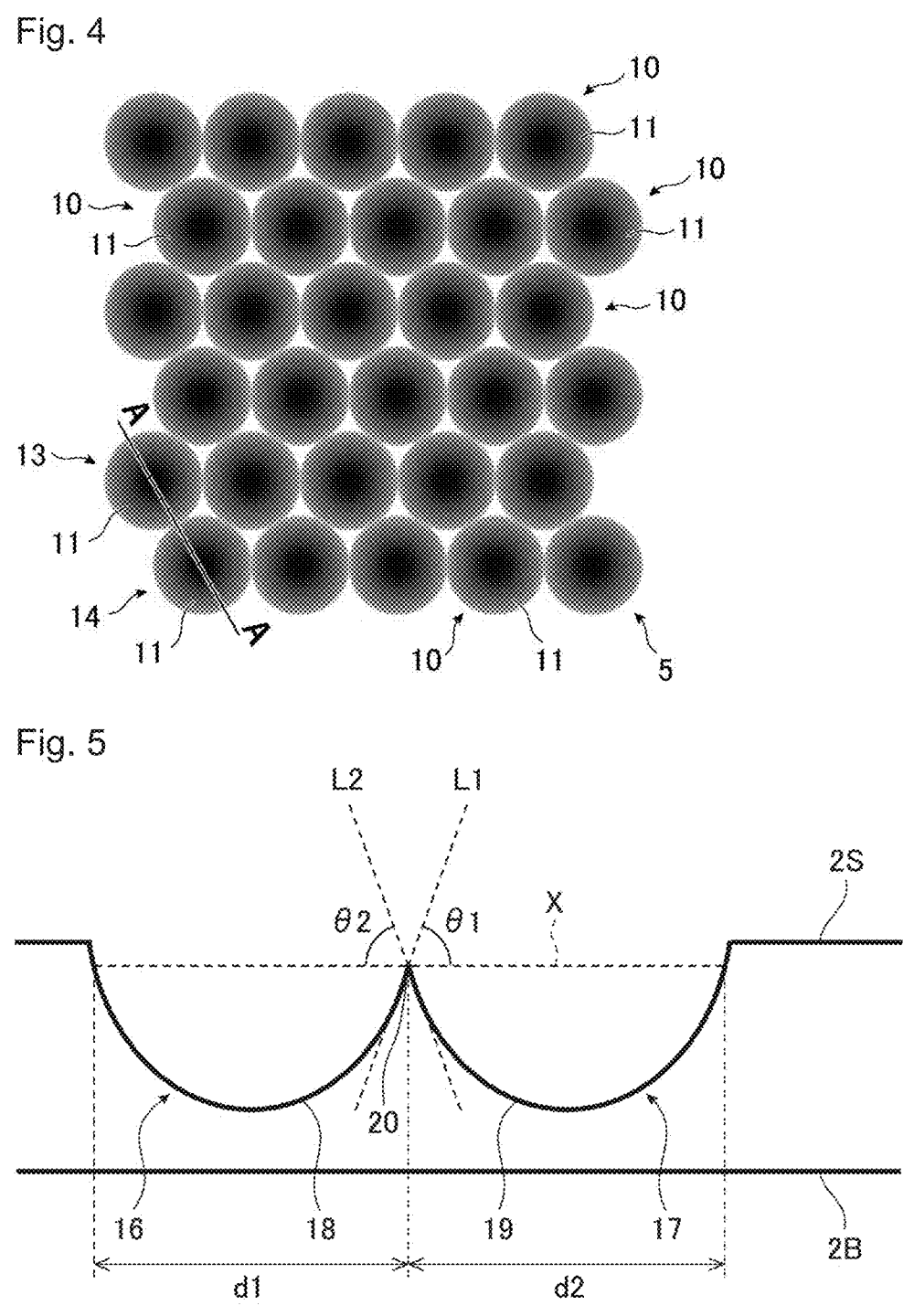

The surface 2S has the same number of the dent-formed regions 5 as the wells 1A. The dent-formed region 5 is a region in which a plurality of dents 10 are formed on the surface 2S, and is provided at certain intervals in the long side direction and in the short side direction of the substrate 2. In the dent-formed region 5, as shown in FIG. 4, a plurality of dents 10 are regularly disposed, for example, in hexagonal or tetragonal alignment at constant intervals. In the dent-formed region 5, with a view to increasing the number of the dents 10 disposed, the distance (pitch) of the two adjacent dents 10 is preferably a relatively small value and is preferably, for example, from 250 μm to 700 μm.

The dent 10 is a dimple formed by eroding or cutting the surface 2S and as shown in FIGS. 3 and 4, has a circular opening 11 at its upper end and has a curved surface 12 surrounding the opening 11. The curved surface 12 rises from the deepest portion of the dent 10, that is from the bottom face, and forms a hemispherical surface or a bent surface other than a spherical surface, specifically, an aspherical surface such as a paraboloidal surface, an ellipsoidal surface or a hyperboloidal surface.

The plurality of dents 10 are formed to have the same shape and the same size, in other words, the size of the opening 11, the radius of curvature of the curved surface 12 at the bottom face, and the depth of the dent 10 are the same among the respective dents 10. The depth of the dent 10 corresponds to a distance from the bottom of the dent to the opening 11.

Since the respective dents 10 are uniform in the shape, the conditions when cells are to be cultured in the dents 10 can be made uniform among the respective dents 10, and the dispersion of the degree of cell growth resulting from the difference in the shape of the dents 10 can be suppressed.

Further, the curved surface 12 of each dent 10 is symmetrical about the center of each dent 10, specifically, the degree of curve (curvature) of the curved surface 12 is substantially constant over 360° around the center. The center of each dent 10 corresponds to the center of the opening 11 which is circular as viewed two-dimensionally.

In the respective dents 10, cells are contained, specifically, spheroids which are aggregates of cells are contained. That is, spheroids are cultured in the dents 10, strictly speaking, cultured in a state immersed in a culture solution stored in the dents 10. Thu number of the spheroids contained in each dent 10 is preferably the same among the dents 1, that is, the spheroids are uniformly distributed in the plurality of the dents 10.

Further, on the surface 2S of the substrate 2, as shown in FIG. 3, a coating film 6 formed of e.g. a cell-non-adhesive polymer such as MPC (2-methacryloyloxyethyl phosphorylcholine) is formed and covers the curved surface 12 of each dent 10 in the dent-formed region 5.

The surface shape of the substrate 2, particularly the shape of the dents 10 will be described in a later section.

The wall member 3 is a plastic injection-molded product. The wall member 3 is, as shown in FIGS. 1 and 2, constituted by tubular partition wall portions 3B disposed inside the outer frame portion 3A connected by a connecting portion 3C extending from the upper periphery of the partition wall portions 3B. The wall member 3 has the same number of the partition wall portions 3B as the dent-formed regions 5 provided on the surface 2S of the substrate 2. Further, in a state where the wall member 3 is fixed to the substrate 2, one partition wall portion 3B is disposed to surround one dent-formed region 5 (see FIG. 2), whereby the space above the dent-formed region 5 is partitioned by the partition wall portion 3B and the well 1A is thereby formed.

The height of the partition wall portion 3B is preferably from 8 to 25 mm, more preferably from 10 to 20 mm.

In the well 1A, as shown from FIGS. 2 and 3, the dent 10 located on the outermost side (that is on the side closet to the partition wall portion 3B) is located slightly away from the inner wall surface of the partition wall portion 3B. In other words, the surface 2S of the substrate 2 has a peripheral region surrounding the dent-formed region 5, and outside the peripheral region 7, the partition wall portion 3B is fixed to the surface 2S of the substrate 2.

<Surface Shape of Substrate>

The surface shape of the substrate 2 will be described in detail below.

In the dent-formed region 5, as shown in FIG. 4, a plurality of dents 10 are densely disposed close to one another. In the example shown in FIG. 4, the distance between centers of two adjacent dents 10, that is the pitch between the dents, is set to be about 540 μm.

The plurality of dents 10 respectively have a depth sufficient to contain cells. The average depth of the dents 10 is, with a view to suppressing drifting of cells (spheroids) out of the dents 10, 200 μm or more, preferably from 200 μm to 550 μm. The depth of the dent 10 is a distance from the opening 11 of the dent 10 to the deepest portion (bottom) of the dent 10. Further, the average depth of the dents 10 is an arithmetic mean obtained from the respective depths of the plurality of dents 10.

The size of the opening 11 and the radius of curvature of the curved surface 12 are preferably set within preferred ranges. For example, the size of the opening 11 is preferably from 250 μm to 700 μm, more preferably from 535 μm to 565 μm. Further, the radius of curvature of the curved surface 12 is preferably about 230 μm. Further, the aspect ratio of each dent 10, that is the ratio of the depth of the dent 10 to the size of the opening 11 is preferably from 0.35 to 1.00, more preferably from 0.35 to 0.80.

Particularly when the size of the opening 11 is from 250 μm to 700 μm and the aspect ratio of the dent 10 is from 0.35 to 0.80, more excellent effects of the present invention will be obtained.

The size of the opening 11 is as follows. In a cut surface of the substrate which passes the centers of the openings of adjacent dents (see after-described FIG. 5), a line is drawn which passes an intersection point (corresponding to the connecting point 20 in FIG. 5) of a nodal line between the curved surface of one of the dents and the cut surface, and a nodal line between the curved surface of the other dent and the cut surface, and which is in parallel with the bottom face 2B of the substrate 2, that is a line corresponding to the base line X in FIG. 5 is drawn. And, the size of the opening 11 means a distance from the intersection point to a point where the line intersects with the nodal line of each dent. In the after-described FIG. 5, the sizes d1 and d2 respectively correspond to the size of the opening 11.

The plurality of dents 10 include two adjacent dents 10. The two adjacent dents 10 are two dents 10 closest to each other. One of the two adjacent dents 10 will be referred to as a first dent 13, and the other will be referred to as a second dent 14. The first dent 13 and the second dent 14 are disposed so that the peripheries of their respective openings 11 are in contact with each other.

When the first dent 13 and the second dent 14 are observed in a cut surface shown in FIG. 5, the curved surfaces 12 of the first dent 13 and the second dent 14 appear on the cut surface as nodal lines 16 and 17 with the cut surface, and the respective nodal lines 16 and 17 are curved lines such as arcs or parabolas as shown in FIG. 5. The cut surface is the A-A face shown in FIG. 4 and is a cut surface of the substrate 2 which passes the center of the opening 11 of the first dent 13 and the center of the opening 11 of the second dent 14.

In a case where the above nodal line indicating the shape of the curved surface 12 is a bent line other than an arc, the shape is approximated by the following polynomial.

$$z = \frac{\dfrac{h^2}{r}}{1 + \sqrt{1 - \dfrac{(1+k)h^2}{r^2}}} + Ah^4 + Bh^6 + Ch^8 + \ldots$$

The above polynomial is a formula to approximate the shape of an aspherical lens, and z represents the sag, h represents the distance from the center, and r represent the radius of curvature. k is the conic coefficient, and is 0 when the curved surface 12 is a spherical surface, is −1 when it is a paraboloidal surface, is a value larger than 0 when it is an ellipsoidal surface, and is a value less than −1 when it is a hyperboloidal surface. A, B and C represent higher order aspheric coefficients.

The nodal line 16 between the cut surface and the first dent 13 has a curved line (hereinafter referred to as first curved line 18) which steeply rises from the bottom of the first dent 13 and extends as curved toward the second dent 14. Likewise, the nodal line 17 between the cut surface and the second dent 14 has a curved line (hereinafter referred to as second curved line 19) which steeply rises from the bottom of the second dent 14 and extends as curved toward the first dent 13.

The first curved line 18 and the second curved line 19 are in contact with each other at their respective upper end positions, that is they are connected at the connecting points 20, as shown in FIG. 5. Further, the first curved line 18 and the second curved line 19 form a bilaterally symmetric shape about a line which passes the connecting point 20 and is perpendicular to the bottom face 2B, as shown in FIG. 5. The shape of each curved line is represented by a radius in a case where the curved line is an arc, and is represented by the above multinomial in a case where the curved line is other than an arc.

Further, as shown in FIG. 5, the inclination angle (hereinafter referred to as angle θ1) of the first tangent line L1 which is in contact with the first curved line 18 and the inclination angle (hereinafter referred to as second angle θ2) of the second tangent line L2 which is in contact with the second curved line 19 are the same. The first tangent line L1 is a tangent line which passes the connecting point 20 and is in contact with the first curved line 18, and the angle θ1 is the degree of the acute angle formed by the base line X which passes the connecting point 20 and is in parallel with the bottom face 2B, and the first tangent line L1. The second tangent line L2 is a tangent line which passes the connecting point 20 and is in contact with the second curved line 19, and the angle θ2 is the degree of the acute angle formed by the base line X and the second tangent line L2. The unit of the angle θ1, θ2 is ° (degree).

And, in the present invention, with a view to appropriately observing the cells in the dents with a microscope, the angles θ1 and θ2 are respectively set so as to satisfy the following formulae (1) and (2).

$$\theta1 < 90 - \theta2 + \sin^{-1}\{\sin(\theta2) \times 1.38/n\} \qquad \text{formula (1)}$$

$$\theta2 < 90 - \theta1 + \sin^{-1}\{\sin(\theta1) \times 1.38/n\} \qquad \text{formula (2)}$$

In the formulae (1) and (2), n is a refractive index of the substrate 2 to light having a wavelength of 540 nm, and is, for example, from 1.51 to 1.52. Such a value is lower than the refractive index (1.59 to 1.60) of polystyrene.

The formulae (1) and (2) are formulae to suppress reflection of light refracted on one of the first dent 13 and the second dent 14 as a virtual image around the other dent, and is delivered from Snell's law.

Specifically, for example, in FIG. 6, with respect to incidence and refraction of light from the culture solution to the dent 10 (for example the second dent 14) of the substrate 2, the following relational expression (3) is satisfied based on Snell's law.

$$ni \times \sin(90 - \theta a) = n \times \sin(\theta b - \theta a) \qquad \text{formula (3)}$$

In the formula (3), ni is the refractive index of the culture solution, particularly, the refractive index to light having a wavelength of 540 nm, the refractive index of the culture solution is substantially equal to the refractive index of water, and ni is about 1.38. Further, (90−θa) is an angle equal the angle of incidence to the curved surface of the dent 10. θa is the angle of an acute angle formed by a base line which passes the position of incidence of the incident light on the curved surface and is in parallel with the base, and the normal to the curved surface of the dent 10 at the position of incidence. θb is an angle of the acute angle formed by the base line and the travelling direction of the light after refracted.

The formula (3) may be modified into the following formula (4).

$$\theta b = \theta a + \sin^{-1}\{\sin(90 - \theta a) \times 1.38/n\} \qquad \text{formula (4)}$$

At the boundary between the first dent 13 and the second dent 14, that is at the connecting point 20, θa=θ2. Thus, if θb>θ1, light refracted on the second dent 14 will not cross the curved surface of the first dent 13 (face corresponding to the first curved line 18) toward the first dent 13, and reflection of refracted light as a virtual image around the first dent 13 can be suppressed.

The above formulae (1) and (2) are delivered as above.

Further, in a case where θ1=θ2, the following formulae (5) and (6) can be delivered in accordance with Snell's law.

$$2\theta1 - \sin^{-1}(\sin(\theta1) \times 1.38/n) < 90 \qquad \text{formula (5)}$$

$$2\theta2 - \sin^{-1}(\sin(\theta2) \times 1.38/n) < 90 \qquad \text{formula (6)}$$

In a case where the dents are uniform in their shape, by the formulae (5) and (6) being satisfied, reflection of refracted light among the dents 10 can be suppressed.

Further, when θ1=θ2, the dents will be uniform in their shape, and such is advantageous in that time for formation of spheroids will also be uniform, and further, the spheroids will be uniform in their size also.

θ1 and θ2 are, in view of more excellent effects of the present invention, preferably from 60 deg to 90 deg, more preferably from 65 deg to 85 deg.

According to the above described surface shape of the substrate 2, particularly the shape of the respective dents 10, cells can appropriately be maintained in the dents 10 and the cells in the dents 10 can appropriately be observed. Specifically, if the depth of the dents 10 is not sufficient, for example, at the time of exchange of the culture solution in the well 1A, the cells in the dents 10 may float up, drift out of the dents 10 and invade into the adjacent dents 10. Whereas in the present invention, since the dents 10 have a depth of 200 μm or more and it is thereby possible to prevent drifting of the cells.

On the other hand, as described above, reflection of refracted light may occur among the adjacent dents 10, and the possibility of reflection of refracted light will be higher as the dents 10 are deeper. Whereas in the present invention, since the respective dents 10 are formed to satisfy the above formulae (1) and (2), reflection of refracted light among the dents 10 can be suppressed even when the depth of the dents 10 is secured.

In the present embodiment, a case where the substrate 2 is constituted by glass is described above, however, as a material constituting the substrate 2, a resin such as polystyrene, polyester, polycarbonate or polyolefin may be used. However, in view of observability with a microscope, the material constituting the substrate 2 is preferably glass, since glass usually has low fluorescence intensity and has high flatness.

As specific examples of glass, soda lime glass, aluminosilicate glass, quartz glass, alkali free glass and borosilicate glass may be mentioned.

In a case where a glass plate is used as the substrate, the coefficient of linear expansion of the glass plate is preferably $9 \times 10^{-7}/°$ C. or less.

In the present embodiment, an example in which a coating film 6 is formed on the surface 2S of the substrate 2 is described above, however, the present invention is not limited to such an example, and the surface 2S of the substrate 2 may not have a coating film 6. However, with a view to forming spheroids of uniform size, a coating film 6 is preferably formed on the surface 2S of the substrate 2.

<Method for Producing Substrate>

Now, a method for producing the substrate 2 of the present invention will be described with reference to a case where the substrate 2 is a glass plate as an example.

First, a glass plate to constitute the substrate 2 is prepared, and to its surface (a surface on which dents are to be formed), a $CO_2$ laser light having a wavelength of 9.6 μm is applied while the angle (full angle) is set to about 20° by a condenser lens, whereby a plurality of seed holes are formed by abrasion on the surface of the glass plate.

The depth of the seed holes may be adjusted for example by $CO_2$ laser irradiation time.

Then, on the surface of the glass plate on which the seed holes are formed, wet etching with hydrofluoric acid, hydrochloric acid or sulfuric acid is applied, whereby the size of the seed holes is gradually increased finally to the size of the dents. As a result, the respective seed holes finally form the dents 10, whereby the substrate 2 of the cell culture container 1 is completed.

The method comprising laser irradiation and wet etching in combination is described as the method for producing the substrate 2 of the present invention, however, the production is not limited thereto, and a method comprising photolithography and wet etching in combination may also be employed.

<Method for Producing Spheroids>

The substrate of a cell culture container of the present invention is suitable as a substrate of a cell culture container to be used for production of spheroids. Spheroids are cell aggregates having human- or animal-derived cells three-dimensionally aggregated.

An example of the method for producing spheroids using the cell culture container 1 of the present invention will be described below. First, a cell suspension containing cells is added to the interior of the well 1A. Once the cells fall into the dents 10, a culture solution in an amount such that the height would be from about 2 to about 5 mm is added to the interior of the well 1A, and the cells contained in the dents 10 are cultured for from several hours to several days, whereby cells grown in the dents 10 are three-dimensionally aggregated to form spheroids.

The cell culture container 1 is preferably subjected to e.g. a sterilization treatment such as EOG sterilization (sterilization with ethylene oxide gas at 60° C.) or autoclave sterilization (sterilization in saturated water vapor at 121° C. for 20 minutes) before use for cell culture.

The culture solution may be further added or exchanged during cell culture.

EXAMPLES

Now, the present invention will be described in further detail with reference to Examples. Ex. 1 and 2 are Examples of the present invention, and Ex. 3 and 4 are Comparative Examples. However, it should be understood that the present invention is by no means restricted to such specific Examples.

Ex. 1

<Preparation of Substrate of Cell Culture Container>

A glass plate was prepared, and to its surface (a surface on which dents were to be formed), a $CO_2$ laser light having a wavelength of 9.6 μm was applied while the angle (full angle) was set to about 20° by a condenser lens, whereby a plurality of seed holes were formed by abrasion on the surface of the glass plate. As the glass plate, "Dragontrail (registered trademark) Pro" (aluminosilicate glass) manufactured by AGC Inc. was used. The refractive index of the glass plate at a wavelength of 540 nm is 1.51.

For formation of the seed holes, the $CO_2$ laser irradiation time was properly set so that the opening size of the seed holes would be 70 μm and the depth would be 460 μm. Further, the $CO_2$ laser irradiation conditions were properly adjusted so that the pitch between the seed holes would be 540 μm.

Then, on the surface of the glass plate on which the seed holes were formed, wet etching with a mixed acid of hydrofluoric acid and hydrochloric acid (hydrofluoric acid concentration: 2 mol/L, hydrochloric acid concentration: 4 mol/L) was applied. Wet etching was conducted until the thickness of the glass plate was decreased by 310 μm. In such a manner, a glass substrate (substrate of a cell culture container) having a plurality of dents formed on its surface was obtained.

Each of the respective dents thus obtained had an opening size of 540 μm and a depth (average depth) of 385 μm. Further, the inclination angles (θ1 and θ2 in FIG. 5) of each of the dents were 70 deg.

On that occasion, the values of the right sides of the formulae (1) and (2) were both 79.2 deg, and thus the relations of the formulae (1) and (2) were satisfied.

Further, the values of the left sides of the formulae (5) and (6) were both 80.8 deg, and thus the relations of the formulae (5) and (6) were satisfied.

Figure 7:
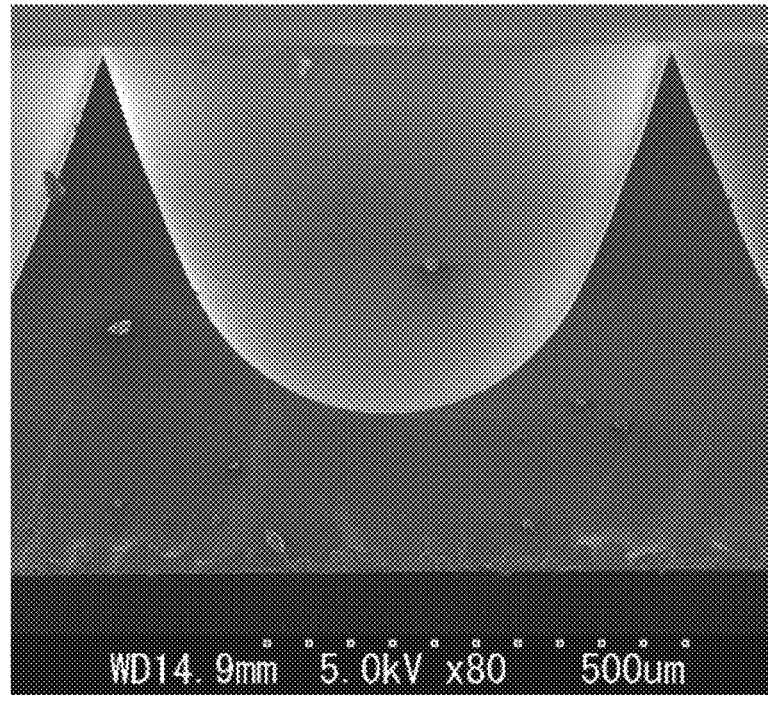
FIG. 7 is an enlarged image of the cross section of the substrate of a cell culture container in Ex. 1 taken by a scanning electron microscope.

The opening size and the average depth of the plurality of dents were determined from an enlarged image with 80 times magnification of a cut surface of the substrate which passed the center of the opening of the first dent and the center of the opening of the second dent among the plurality of dents, observed with a field emission scanning electron microscope "S-4300" manufactured by Hitachi High-Tech Corporation. An enlarged image of a cut surface of the substrate of a cell culture container in Ex. 1 obtained in such a manner is shown in FIG. 7.

In the after-described Ex., the opening size and the average depth of the plurality of dents were measured in the same manner as in Ex. 1.

<Preparation of Cell Culture Container>

An adhesive "SE9140RTV" manufactured by DOW TORAY CO., LTD. was applied to the bottom face of a wall member (injection molded product made of polystyrene, see the wall member 3 in FIG. 1), using a dispenser "JETMASTER" manufactured by Musashi Engineering, Inc.

Then, the surface of the wall member coated with the adhesive, and the surface of the substrate of a cell culture container having the dents formed, were overlaid and contact-bonded, and air-dried for 12 hours, whereby a cell culture container having the structure as shown in FIGS. 1 and 2 was obtained.

<Preparation of Spheroids>

In the well of the prepared cell culture container, 25 μL of a medium comprising "E-MEM" and 10 vol % of fetal bovine serum "FBS" added, was dropped by a pipette, and to remove bubbles in the dents, centrifugal treatment was conducted for 10 minutes at a centrifugal force of 750×g by a centrifuge.

Then, in the well, 50 μm of a suspension of hepatocellular carcinoma "HepG2" cells was dropped by a pipet, and centrifugal treatment was conducted for 1 minute at a centrifugal force of 200×g by a centrifuge. The suspension contains 22,500 HepG2 cells.

Then, the cell culture container was left at rest in a $CO_2$ incubator at 37° C. under 5 vol % $CO_2$ conditions for 4 days to culture the cells thereby to obtain spheroids.

Ex. 2

<Preparation of Substrate of Cell Culture Container>

A photoresist was applied by a die coater on one surface of a glass plate "Dragontrail (registered trademark) Pro" manufactured by AGC Inc. to form a photoresist film. As the photoresist, "Glibes N-100 PT 23000P" (trade name) manufactured by TOKYO OHKA KOGYO CO., LTD. was used.

Then, using a photomask such that the portion to be exposed would have a pattern with a diameter of 70 μm and a pitch of 540 μm, ultraviolet light having a wavelength of 365 nm was applied to expose the photoresist film, and then a development treatment was conducted to remove the photoresist film at the exposed portion.

Then, wet etching was conducted with a mixed acid of hydrofluoric acid and hydrochloric acid (hydrofluoric acid concentration: 2 mol/L, hydrochloric acid concentration: 4 mol/L), by which hydrofluoric acid and hydrochloric acid as the wet etching liquid infiltrate into holes having a diameter of 70 μm formed by the photoresist film being removed, whereby a plurality of hemispherical holes (dents) were formed on the glass, starting from the holes. Wet etching was conducted until the average depth of the plurality of dents reached 260 μm, and finally, the photoresist was removed with a release agent.

In such a manner, a glass substrate (substrate of a cell culture container) having a plurality of dents formed on its surface was obtained.

Each of the respective dents thus obtained had an opening size of 540 μm and a depth (average depth) of 200 μm. Further, the inclination angles ($\theta 1$ and $\theta 2$ in FIG. 5) of each of the dents were 75 deg.

On that occasion, the values of the right sides of the formulae (1) and (2) were both 77.0 deg, and thus the relations of the formulae (1) and (2) were satisfied.

Further, the values of the left sides of the formulae (5) and (6) were both 88.0 deg, and thus the relations of the formulae (5) and (6) were satisfied.

<Preparation of Cell Culture Container>

A cell culture container in Ex. 2 was obtained in the same manner as in the preparation of the cell culture container in Ex. 1 except that the substrate of a cell culture container in Ex. 2 was used.

<Preparation of Spheroids>

Spheroids were obtained in the same manner as in the preparation of spheroids in Ex. 1 except that the cell culture container in Ex. 2 was used.

Ex. 3

<Preparation of Substrate of Cell Culture Container>

A glass plate was prepared, and to its surface (a surface on which dents were to be formed), a $CO_2$ laser light having a wavelength of 9.6 μm was applied while the angle (full angle) was set to about 20° by a condenser lens, whereby a plurality of seed holes were formed by abrasion on the surface of the glass plate. As the glass plate, "Dragontrail (registered trademark) Star" manufactured by AGC Inc. was used. The refractive index of the glass plate at a wavelength of 540 nm is 1.51.

For formation of the seed holes, the $CO_2$ laser irradiation time was properly set so that the opening size of the seed hole would be 70 μm and the depth would be 560 μm. Further, the $CO_2$ laser irradiation conditions were properly adjusted so that the pitch between the seed holes would be 520 μm.

Then, on the surface of the glass plate on which the seed holes were formed, wet etching with a mixed acid of hydrofluoric acid and hydrochloric acid (hydrofluoric acid concentration: 2 mol/L, hydrochloric acid concentration: 4 mol/L) was applied. Wet etching was conducted until the thickness of the glass plate was decreased by 360 μm. In such a manner, a glass substrate (substrate of a cell culture container) having a plurality of dents formed on its surface was obtained.

Each of the respective dents thus obtained had an opening size of 520 μm and a depth (average depth) of 510 μm. Further, the inclination angles ($\theta 1$ and $\theta 2$ in FIG. 5) of each of the dents were 80 deg.

On that occasion, the values of the right sides of the formulae (1) and (2) were both 74.2 deg, and thus the relations of the formulae (1) and (2) were not satisfied.

Further, the values of the left sides of the formulae (5) and (6) were both 95.8 deg, and thus the relations of the formulae (5) and (6) were not satisfied.

<Preparation of Cell Culture Container>

A cell culture container in Ex. 3 was obtained in the same manner as in the preparation of the cell culture container in Ex. 1 except that the substrate of a cell culture container in Ex. 3 was used.

<Preparation of Spheroids>

Spheroids were obtained in the same manner as in the preparation of spheroids in Ex. 1 except that the cell culture container in Ex. 3 was used.

Ex. 4

<Preparation of Substrate of Cell Culture Container>

A mold having a plurality of hemispherical protrusions having a diameter of 560 μm and a heigh of 400 μm was prepared by a mold processing machine. Using the obtained mold, polystyrene was injection-molded to prepare a polystyrene substrate (substrate of cell culture container) having a plurality of dents formed thereon, having a shape reverse to the mold. The refractive index of the polystyrene at a wavelength of 540 nm is 1.59.

The plurality of dents thus obtained had an opening size of 560 μm and a depth (average depth) of 400 μm. Further, the inclination angles ($\theta 1$ and $\theta 2$ in FIG. 5) of each of the dents were 80 deg.

On that occasion, the values of the right sides of the formulae (1) and (2) were both 68.7 deg, and thus the relations of the formulae (1) and (2) were not satisfied.

Further, the values of the left sides of the formulae (5) and (6) were both 101.3 deg, and thus the relations of the formulae (5) and (6) were not satisfied.

<Preparation of Cell Culture Container>

A cell culture container in Ex. 4 was obtained in the same manner as in the preparation of the cell culture container in Ex. 1 except that the substrate of a cell culture container in Ex. 4 was used.

<Preparation of Spheroids>

Spheroids were obtained in the same manner as in the preparation of spheroids in Ex. 1 except that the cell culture container in Ex. 4 was used.

[Evaluation Test]

<Evaluation of Spheroid Maintaining Property and Observability>

Using an inverted microscope "Axio Observer" manufactured by ZEISS, with a 5 times magnification object lens, the dent-formed region at the well bottom face in the cell culture container in each Ex. and the spheroids in the dents were observed to evaluate the spheroid maintaining properties in the dents and the observability of spheroids in the dents based on the following evaluation standards. The evaluation results are shown in Table 1.

Figure 8:
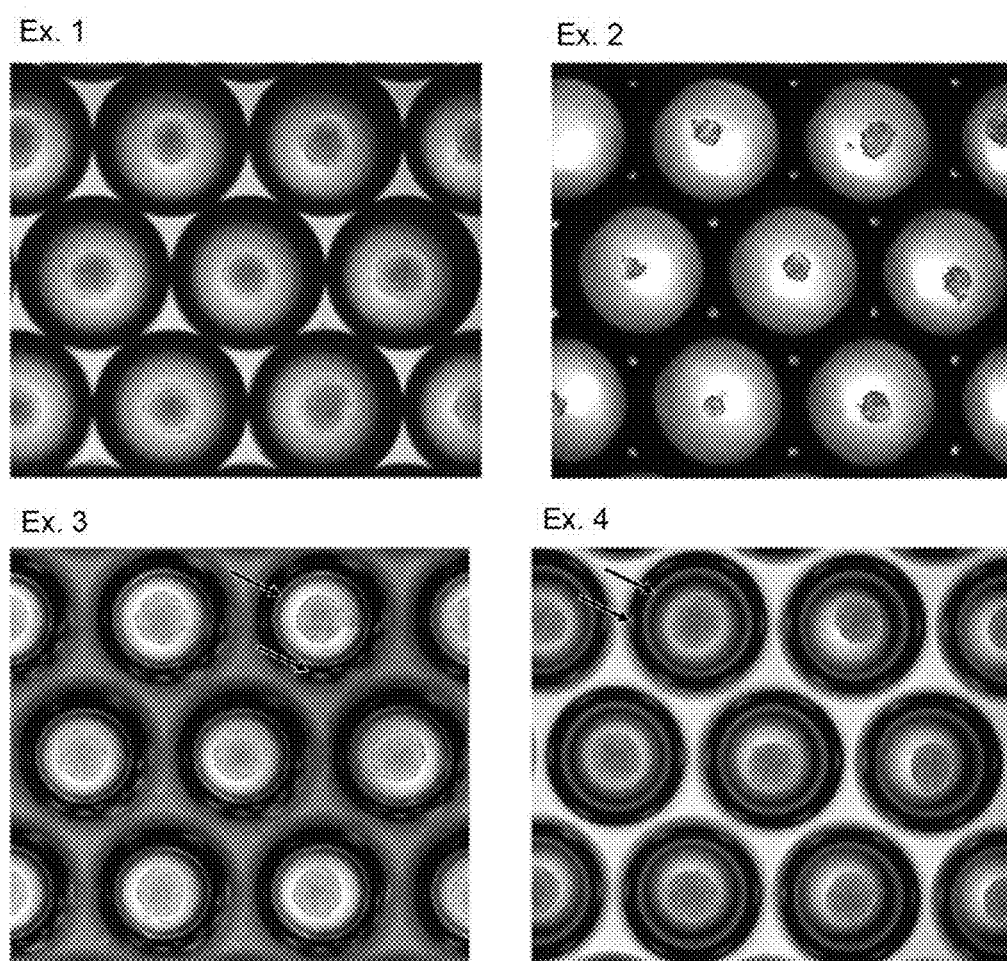
FIG. 8 is images of the dent-formed regions in Ex. observed with an inverted microscope.

Images of the dent-formed region in each Ex. observed with the inverted microscope are shown in FIG. 8. Portions indicated by arrows in Ex. 3 and 4 correspond virtual images (reflection).

In Ex. 1 to 3, cell culture was carried out in the cell culture container of the present invention, however, it is also possible that cell culture is carried out in another container and the cultured cells are put in the container in each of Ex. 1 to 3, and thus the container is used only for observation. Such may be done particularly in the field of drug discovery screening.

(Standards for Evaluation of Spheroid Maintaining Property)

A: Spheroids are appropriately maintained in the dents.

B: Spheroids drift out of the dents.

(Standards for Evaluation of Observability of Spheroids in Dents)

A: No virtual image (reflection) occurs around the dents, and spheroids are easily observed.

B: Virtual image (reflection) occurs around the dents, and spheroids are hardly observed.

TABLE 1

| | Type of substrate | Refractive index of substrate | Opening size of dent (unit: μm) | Average depth of dent (unit: μm) | Inclination angle of dent (θ1, θ2) (unit: deg) | Right side value of formula (1), (2) (unit: deg) | Left side value of formula (5), (6) (unit: deg) | Evaluation results Maintaining property | Observability |
|---|---|---|---|---|---|---|---|---|---|
| Ex. 1 | Dragontrail Pro | 1.51 | 540 | 385 | 70 | 79.2 | 80.8 | A | A |
| Ex. 2 | Dragontrail Pro | 1.51 | 540 | 200 | 75 | 77.0 | 88.0 | A | A |
| Ex. 3 | Dragontrail Star | 1.51 | 520 | 510 | 80 | 74.2 | 95.8 | A | B |
| Ex. 4 | Polystyrene | 1.59 | 560 | 400 | 80 | 68.7 | 101.3 | A | B |

It was confirmed from Table 1 that by using the substrate of a cell culture container of the present invention, cells can appropriately be maintained in the dents, and the cells in the dents can appropriately be observed (Ex. 1 and 2).

The entire disclosure of Japanese Patent Application No. 2022-017367 filed on Feb. 7, 2022 including specification, claims, drawings and summary is incorporated herein by reference in its entirety.

REFERENCE SYMBOLS

1: cell culture container
1A: well
2: substrate
2B: bottom face
2S: surface
3: wall member
3A: outer frame portion
3B: partition wall portion
3C: connecting portion
4: adhesive layer
5: dent-formed region
6: coating film
7: peripheral region
10: dent
11: opening
12: curved surface
13: first dent
14: second dent
16,17: nodal line
18: first curved line
19: second curved line
20: connecting point
L1: first tangent line
L2: second tangent line
X: base line
d1,d2: size

What is claimed is:

1. A substrate of a cell culture container, having a bottom face and a surface provided on the opposite side from the bottom face, wherein the surface has a dent-formed region having a plurality of dents formed, an average depth of the plurality of dents is 200 μm or more, the plurality of dents includes a first dent and a second dent adjacent to each other, a nodal line of a cut surface of the substrate which passes the center of an opening of the first dent and the center of an opening of the second dent, and the first dent, has a first curved line which rises from the bottom of the first dent and extends as curved toward the second dent, the nodal line of the cut surface and the second dent has a second curved line which rises from the bottom of the second dent and extends as curved toward the first dent, the first curved line and the second curved line are connected at a connecting point, the following formula (1) is satisfied wherein θ1 (deg) is an angle formed by a first tangent line which passes the connecting point and which is in contact with the first curved line, and a base line which passes the connecting point and which is in parallel with the bottom face, and n is a refractive index of the substrate to light having a wavelength of 540 nm, and the following formula (2) is satisfied wherein θ2 (deg) is an angle formed by a second tangent line which passes the connecting point and which is in contact with the second curved line, and the base line:

$$\theta_1 < 90 - \theta_2 + \sin^{-1}\{\sin(\theta_2) \times 1.38/n\} \qquad \text{formula (1)}$$

$$\theta_2 < 90 - \theta_1 + \sin^{-1}\{\sin(\theta_1) \times 1.38/n\} \qquad \text{formula (2)}.$$

2. The substrate of a cell culture container according to claim 1, which is constituted by glass.

3. The substrate of a cell culture container according to claim 1, wherein a size of opening of each of the plurality of dents is from 250 μm to 700 μm, and a ratio of a depth of the dent to the size of the opening of each of the plurality of dents is from 0.35 to 0.80.

4. The substrate of a cell culture container according to claim 1, wherein the angle θ1 and the angle θ2 are the same.

5. A cell culture container, which comprises the substrate of a cell culture container as defined in claim 1, and a wall member which is fixed at a position surrounding the dent-formed region on the substrate and which separates a space above the dent-formed region.

* * * * *